(12) United States Patent
Nuyan et al.

(10) Patent No.: US 8,930,007 B2
(45) Date of Patent: Jan. 6, 2015

(54) METHOD OF MODELING THE COLORING PROCESS IN MOVING WEB MANUFACTURING

(75) Inventors: Seyhan Nuyan, Duluth, GA (US); Calvin Fu, Concord (CA); Tommi Loyttyniemi, Tampere (FI)

(73) Assignee: Metso Automation Inc., Vantaa (FI)

( * ) Notice: Subject to any disclaimer, the term of this patent is extended or adjusted under 35 U.S.C. 154(b) by 128 days.

(21) Appl. No.: 13/639,736

(22) PCT Filed: Apr. 8, 2010

(86) PCT No.: PCT/US2010/030375
§ 371 (c)(1),
(2), (4) Date: Dec. 17, 2012

(87) PCT Pub. No.: WO2011/126486
PCT Pub. Date: Oct. 13, 2011

(65) Prior Publication Data
US 2013/0096707 A1 Apr. 18, 2013

(51) Int. Cl.
*G06F 19/00* (2011.01)
*G06F 17/50* (2006.01)
*G01N 21/86* (2006.01)

(52) U.S. Cl.
CPC ............... *G06F 17/50* (2013.01); *G01N 21/86* (2013.01)
USPC .......................................................... 700/97

(58) Field of Classification Search
CPC ...... G06Q 10/06; G06Q 10/087; G06F 17/50; G05B 19/41865; G05B 19/4097
USPC .......................................................... 700/97
See application file for complete search history.

(56) References Cited

U.S. PATENT DOCUMENTS

| 4,439,038 | A | 3/1984 | MacTaggart |
| 5,047,652 | A | 9/1991 | Lisnyansky et al. |
| 5,082,529 | A | 1/1992 | Burk |
| 6,052,194 | A | 4/2000 | Nuyan |
| 6,263,291 | B1 | 7/2001 | Shakespeare et al. |
| 6,721,692 | B2 | 4/2004 | Mestha et al. |

OTHER PUBLICATIONS

International Search Report issued in International Application No. PCT/US2010/030375 dated Jun. 4, 2010.
Written Opinion of the International Searching Authority issued in International Application No. PCT/US2010/030375 dated Jun. 4, 2010.
International Search Report dated Aug. 22, 2013 issued in European Patent Application No. 10849591.2.
Industrial Color Testing Fundamentals and Techniques (Second Edition), Wiley-VCH, pp. 98, 115-116 Jan. 1, 2001.

*Primary Examiner* — Tarifur Chowdhury
*Assistant Examiner* — Md Rahman
(74) *Attorney, Agent, or Firm* — Oliff PLC

(57) ABSTRACT

A method and apparatus are set forth for modeling a coloring process in moving web manufacturing through dye response gain adaptation using measured sheet color spectrum; and dye response shape adaptation using measured color spectrum of the production sheet. The adaptation of colorant (dye) response gain uses the measured sheet color spectrum value at the value of maximum light absorbance of the dye. The adaptation of dye response spectrum uses the measured sheet color reflectance spectrum and sample sheet color spectrum with a corresponding response shape calculated using a formula to adapt the current sheet condition dye response shape using the dye response from the sample sheet on the assumption of a constant ratio of absorption change to dye concentration change.

18 Claims, 6 Drawing Sheets

METHOD OF MODELING THE COLORING PROCESS IN MOVING WEB MANUFACTURING

FIELD

The present specification relates to the manufacture of rolls, and more particularly to a method and apparatus for modeling the coloring process in moving paper web manufacturing for optimum control of sheet color with colorants and optical brightening agents.

BACKGROUND

Tinting and/or coloring paper by the use of colorants, such as dyes and optical brightening agents (OBAs) has been common for many years in the operation of paper making machines. The actual sheet or web color is determined by measuring the reflectance spectrum of the web sheet as it travels through the production process. For example, measurement may be performed by an online spectrophotometer that measures the reflectance spectrum of the sheet. Dye additions can be made at different stages of the paper making process to achieve a desired color shade.

The spectrophotometer is typically mounted to a scanning device for continuously measuring sheet color reflectance spectrum from a standard light source that is directed at one side of the sheet, with a backing background on the opposite side of the sheet chosen for reducing opacity effects. The measured sheet reflectance spectrum range is typically from 360 to 720 nm in wavelength, covering the range of visible light wavelengths plus a portion of the ultra-violet spectrum. By using a set of standard non-linear equations, the sheet reflectance spectrum can be used to calculate sheet color in terms of various defined coordinate systems, for example CIE L*, a*, b* values, where L* represents a lightness axis ranging from 0 for black and 100 for white, a* represents a red-green axis where a positive number is indicative of redness while a negative number is indicative of greenness, and b* represents a blue-yellow axis where a positive number is indicative of yellowness while a negative number is indicative of more blueness.

Control of the sheet color using a set of dyes requires knowledge of the response model for each dye, which is typically represented by sheet color reflectance spectrum value change given a normalized dye flow ratio change, for example, pound-per-ton of fiber stock used to make the paper. With knowledge of the sheet target value ($L_t$, $a_t$, $b_t$) and measured sheet value ($L_m$, $a_m$, $b_m$) and the response model for each dye, a control algorithm can be used to calculate the dye flow ratio change for minimizing sheet color error from the target value, normally represented by $\Delta E$, as follows: $\Delta E=\mathrm{sqrt}[(L_t-L_m)^2+(a_t-a_m)^2+(b_t-b_m)^2]$.

The dye response model (i.e. reflectance spectrum value change per unit dye ratio change) is normally obtained through the use of a "bump" test. For example, under normal operating conditions with manual color control and a stable production process, the measured sheet reflectance spectrum value change is calculated before and after a dye ratio change and the normalized spectrum difference is used for the dye response model. This model has been found to be valid for paper production of similar sheet color as produced during the "bump" test.

Color changes made during the production of paper often result in 'off-spec' sheet material being produced, both during and after such color changes. This 'off-spec' web, referred to as color broke, is typically recycled back to the early stages of production. Accordingly, one of the goals in sheet color control is to develop an accurate dye response model that quickly minimizes the error between the measured sheet color and the target color, thereby reducing the occurrence of sheets that are off-specification during and following a grade change or at start-up or as a result of disturbances that may occur during steady-state, and thereby also reducing costs.

It is also known in the prior art to model the steady state behaviour of the coloring process by determining a steady state gain from the dye flow to the measured color at different concentrations, or by spectral response models obtained by dye response tests. One example of dye response model gain adaptation is described in U.S. Pat. No. 6,052,194 (Nuyan), the contents of which are incorporated herein by reference. In either dye response model gain adaptation or spectral response modelling, the resulting model is grade-dependent. This grade dependency is especially severe in the case of dye response model gain adaptation because of the highly non-linear relationship of measured color to the measured sheet spectrum.

The dye response model, described above, can be decomposed into a normalized response shape over the spectrum range (360 to 720 nm, with unit gain), and associated with a response gain (i.e. a scalar) for gain adaptation by creating a non-linear table of actual dye flow ratio used and the associated response gain, while keeping the response shape constant. The non-linear table may be calculated using a series of bump tests during the production process using different dye ratios. When using this type of gain adaptation, a base flow must be added to the actual dye flow in order to represent an "equivalent" amount of dye in the broke stock.

The model gain and base flow relation is highly non-linear. For instance, the gain difference could be as high as several thousand folds when producing light shade color (normally low dosage of dye) and dark shade color (normally high dosage) of paper. To get an accurate relation of gain-base flow curve, many "bump" tests were needed.

There are at least two issues that have limited the use of the dye response model gain adaptation set forth above. First, it has been observed that when producing a deep shade color paper, the actual dye response gain is significantly smaller than when producing light shade color paper for the same dye using a similar dye ratio. Second, when a large amount of broke is used as furnish, there is no accurate way to estimate the corresponding base flow (added offset of a dye flow) of the dye. It has been reported that the amount of broke can be as high as 80% in extreme cases.

Furthermore, it has been discovered that the dye response shape over the spectrum can depend on the measured sheet color, especially when the sheet color shade is dark. The difference can in some circumstances be so large that the resulting control action is in the opposite direction to the predicted response based on dye flows.

SUMMARY

A method is set forth in greater detail below for modeling the coloring process in moving web manufacturing for optimum control with dyes and optical brightening agents (OBA's). The method does not require the traditional on-line step response tests (bump tests) and relies only on the measured reflectance spectrum of the moving web and on predetermined spectral reflectance data of a set of sample sheets (normally provided by dye suppliers and stored in the color control system).

According to one aspect of this specification, there is provided a color modeling process for use in manufacturing a colored material, comprising a-priori measuring of the reflectance spectra of sample materials covering a range of production colors and determining therefrom a model; and on-line measuring of the reflectance spectrum of said colored material and applying said model thereto for at least one of predicting color trajectory or generating control actions to regulate the flow of at least one of a colorant or optical brightening agent.

According to another aspect, there is provided a color control process for use in color paper web manufacturing, comprising a-priori measuring of the reflectance spectra of sample sheets covering a range of known concentrations of at least one of a colorant or optical brightening agent and determining therefrom a model; and on-line measuring of the reflectance spectrum of said color paper web and applying said model thereto for generating control actions to regulate the flow of said at least one of a colorant or optical brightening agent applied to the color web for achieving a target color or brightness.

According to a further aspect, there is provided an apparatus for controlling the color of a web of paper, comprising a spectrophotometer for scanning said web of paper; a plurality of regulators; and a color controller connected to said spectrophotometer and regulators for a-priori measuring of the reflectance spectra of sample sheets covering a range of known concentrations of at least one of a colorant or optical brightening agent and determining therefrom a model, and on-line measuring of the reflectance spectrum of said color paper web and applying said model thereto for generating and transmitting control actions to said a plurality of regulators for regulating the flow of said at least one of a colorant or optical brightening agent applied to the color web for achieving a target color or brightness.

For each colorant, a set of color samples is provided with different known dye ratios to the pulp, as well as a "white" sample with no dye added. The sheet reflectance spectrum is measured (off-line) for each color sample and the white sample. For each dye, a 'dye absorption wavelength' is identified from the measured reflectance spectrum samples at which the reflectance spectrum value is minimum. During the production process (i.e. on-line) the measured sheet color reflectance spectrum value and the dye absorption wavelength are used for colorant model response shape and gain adaptation. The adaptation table is generated from the samples, as follows: for given samples "A" and "B", the dye response is (spectrum of sample A−spectrum of sample B)/(concentration of sample A−concentration of sample B). The normalized result spectrum (normalized on a scale of −1 to 0) comprises the dye response shape and the associated multiplying factor comprises the dye response gain. The adaptation point is based on the average spectrum value of sample A and sample B at the dye absorption wavelength. When the measured sheet reflectance spectrum value at the absorption wavelength falls between two adaptation points, a weighted interpolation is used to generate both the color model response shape and the response gain.

The method set forth above can also be applied when "tinting" the moving web with colorants, for example by adding a blue colorant to a red sheet or adding a small amount of yellow colorant to a deep shade of blue sheet. Additional method steps are set forth to reduce the set of response models generated as described above into a fundamental model set from which the applicable response is generated adaptively using the measured color spectrum.

According to another aspect of the specification, the construction of adaptive response gains is set forth where the adaptation is based on the previous control actions and their measured effects in the reflectance spectrum of the sheet, for fast color changes required when the manufacturer makes color grade changes. For example, when full control results in the measured sheet color changing toward the target by only a fraction of the full distance (ΔE) in the color (L, a, b) space as compared with the predicted change, the model gain can be reduced for more aggressive color change. This can account for dye retention differences at the initial stage of producing a dark paper grade (i.e. a sheet with small L value). Such aggressive adaptation is not typically necessary when the production stabilizes near its color target.

BRIEF DESCRIPTION OF THE DRAWINGS

Exemplary embodiments will be better understood with reference to the following FIGS in which like numerals denote like parts and in which:

FIGS. 3A-3C are schematic representations of an exemplary set of dye response gains and response spectra for a typical red dye sample sheet, wherein FIG. 3A shows reflectance spectra of a sample sheet using different red dye concentration and of a white base sheet, FIG. 3B shows reflectance spectra difference normalized with respect to concentration difference from the white base sheet (i.e. spectrum difference per unit change in colorant), and FIG. 3C shows reflectance spectra difference normalized using two different samples of similar color shade (for examples: using 200 lb sample and 400 lb. sample, or using 8 lb sample or 15 lb. sample);

DETAILED DESCRIPTION

Figure 1:
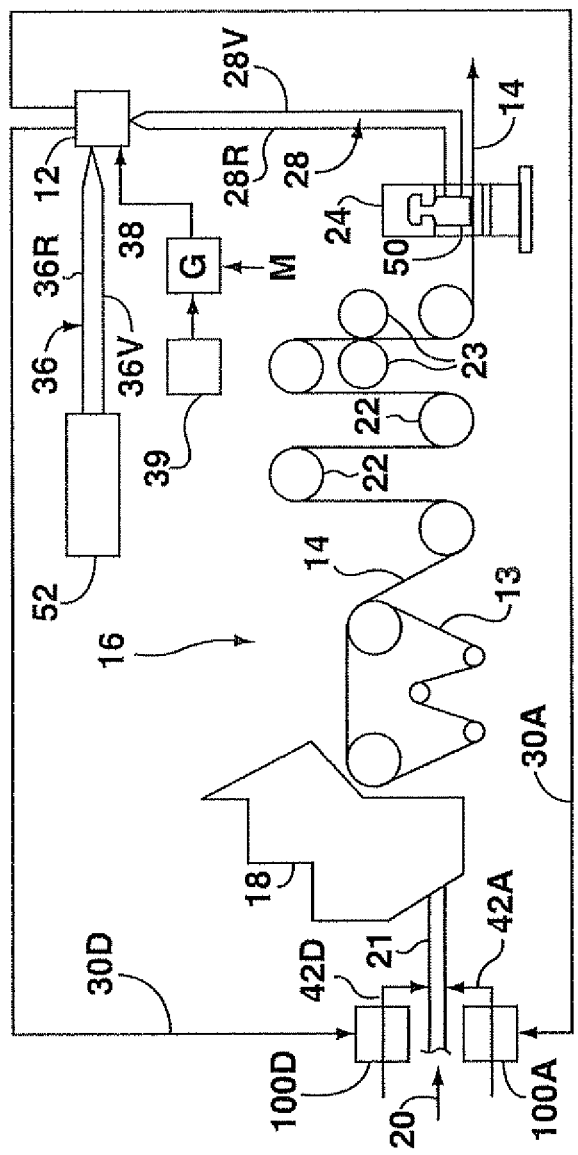
FIG. 1 is a schematic representation of a machine for making colored paper that incorporates a controller for modeling the coloring process according to an exemplary embodiment.

Turning to FIG. 1 of the drawings, a color controller 12 controls the color of a web of paper 14 produced by a paper machine indicated by the reference numeral 16. Paper machine 16 includes a headbox 18 that discharges a wet paper web 14 from a slurry of pulp 20 which flows through pipe 21 to headbox 18. Web 14 is initially supported by a porous belt 13 and acquires strength and form as it passes along rollers 22 to a pair of opposed press rollers 23 which may be used for surface sizing or for pigmented surface coatings. Web 14 eventually passes through a frame 24 along which a spectrophotometer 50 scans the width of paper web 14.

Spectrophotometer 50 uses a light source to light the web 14. Light reflected by the web passes to a grating that splits the light into the full spectrum of colors. The spectrum of light impinges upon a diode array that measures the amount of light at each wavelength. The spectral data is sent to controller 12 in the form of measured reflectance signals (indicated generally by the reference numeral 28) taken at a number of wavelength bands, typically seventy two, spanning the visible spectrum (e.g. 360 to 720 nm wavelength in 5 nm intervals). This spectral data may, for example, be expressed as X, Y, Z tristimulus colorimeter values. However, because X, Y and Z values are not easily understood in terms of object color, other color scales have been developed to simplify understanding, improve communication of color differences and which are more linear throughout color space. As discussed above, one example of such a color scale is the CIE L*, a*, b* color space, which is mathematically derived from the X, Y, Z values, and where L* represents a lightness axis, a* represents a red-green axis and b* represents a blue-yellow axis, according to opponent-colors theory.

The measured spectral data is multiplied together with target reflectance values indicated generally by the reference numeral 36 and stored in memory 52, representing dye response gain and dye response spectrum shape for each sample. Non-linear equations representing color gain in the measured color spectrum are used to calculate the gradients and direction directives in the color control optimization, as discussed in greater detail below. Any number of dyes can be used for the color control (but typically the number of dyes used is 1 to 4).

Controller 12 generates dye flow control signals 30D and additive flow control signals 30A. Independently controlled indexers 39 provide signals which are coupled through gates 38 to controller 12 to change the flow of additives applied to the web 14. A signal M enables gates 38 at certain times for metering the flow of additives.

In response to dye flow control signals 30D from controller 12, dye flow regulators 100D dispense dyes 42D to control the color of web 14. In response to additive flow control signals 30A, additive regulator 100A dispenses controlled volumes of additives 42A that affect other qualities of paper web 14.

As described in greater detail below, two new aspects of color control are provided by controller 12: dye response gain adaptation using measured sheet color spectrum value at the dye absorption wavelength; and dye response shape adaptation using measured color spectrum of the production sheet.

Having regard to the former, the adaptation of colorant (dye) response gain uses the measured sheet color spectrum value at the value of maximum light absorbance of the dye. This wavelength is referred to herein as the dye absorption wavelength, which can be identified from sample sheets as the most negative point in the reflectance spectrum difference between a colorant sample sheet and a white base sheet. This wavelength is usually the same for all samples using the same dye with different dye concentrations.

Having regard to the latter, it has been discovered that when a dye concentration changes, its influence is linear in ratio of light absorption to scattering rather than in light reflectance. More particularly, the relation is highly non-linear for deep shade color sheets but has close-to-linear relation for light shade colour sheet (i.e. the relation between the color sensed by spectrophotometer 50 as represented by light reflectance to light absorption is highly non-linear when the sheet color is dark). The adaptation of dye response spectrum therefore uses the measured sheet color reflectance spectrum and the sample sheet color spectrum with a corresponding response shape calculated using a formula to adapt the current sheet condition dye response shape using the dye response from the sample sheet on the assumption of a constant ratio of absorption change to dye concentration change.

Figure 2:
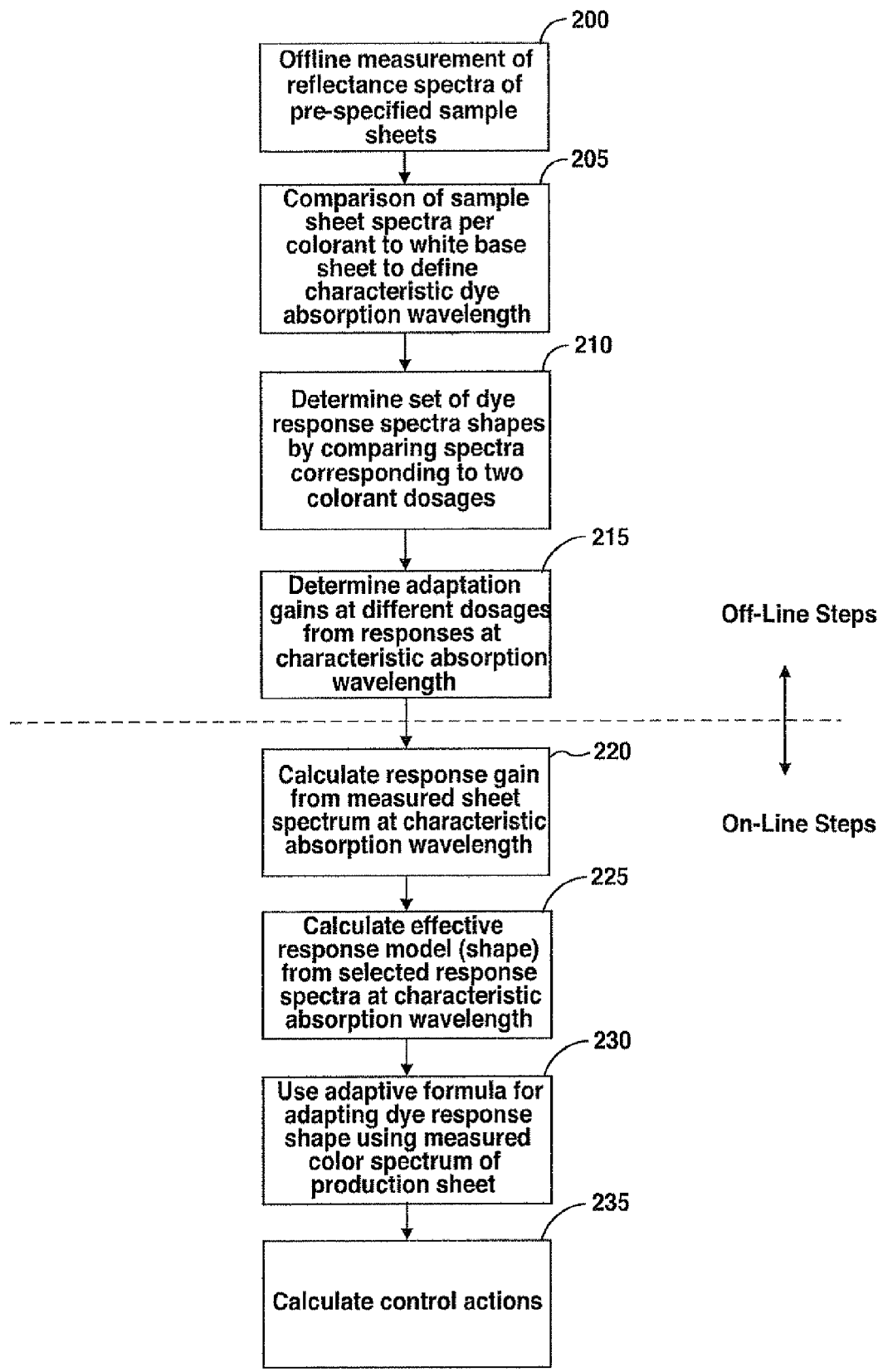
FIG. 2 is a flowchart showing a method for effecting the coloring process using the controller of FIG. 1, according to an exemplary embodiment
Figure 3A:
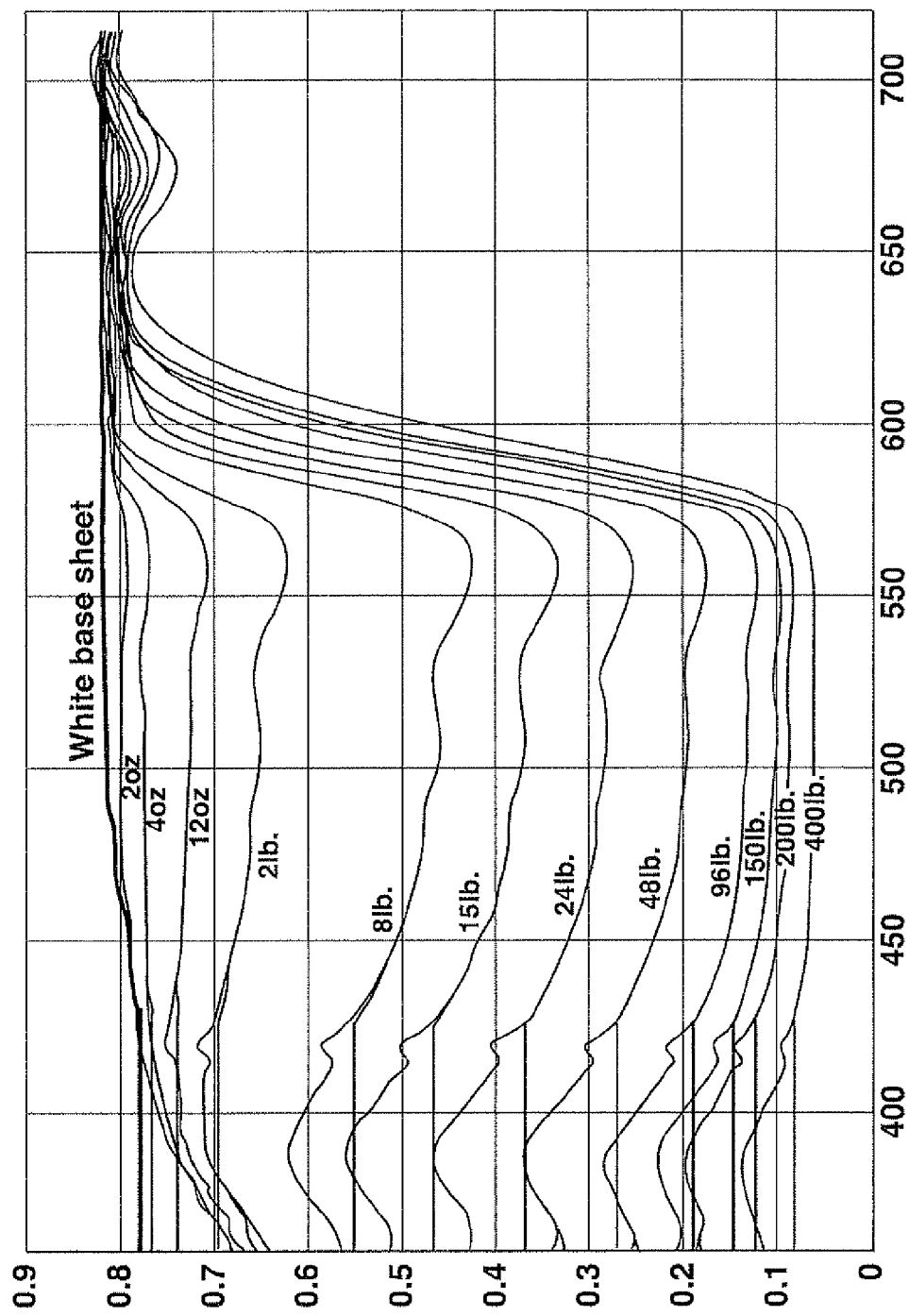
Figure 3B:
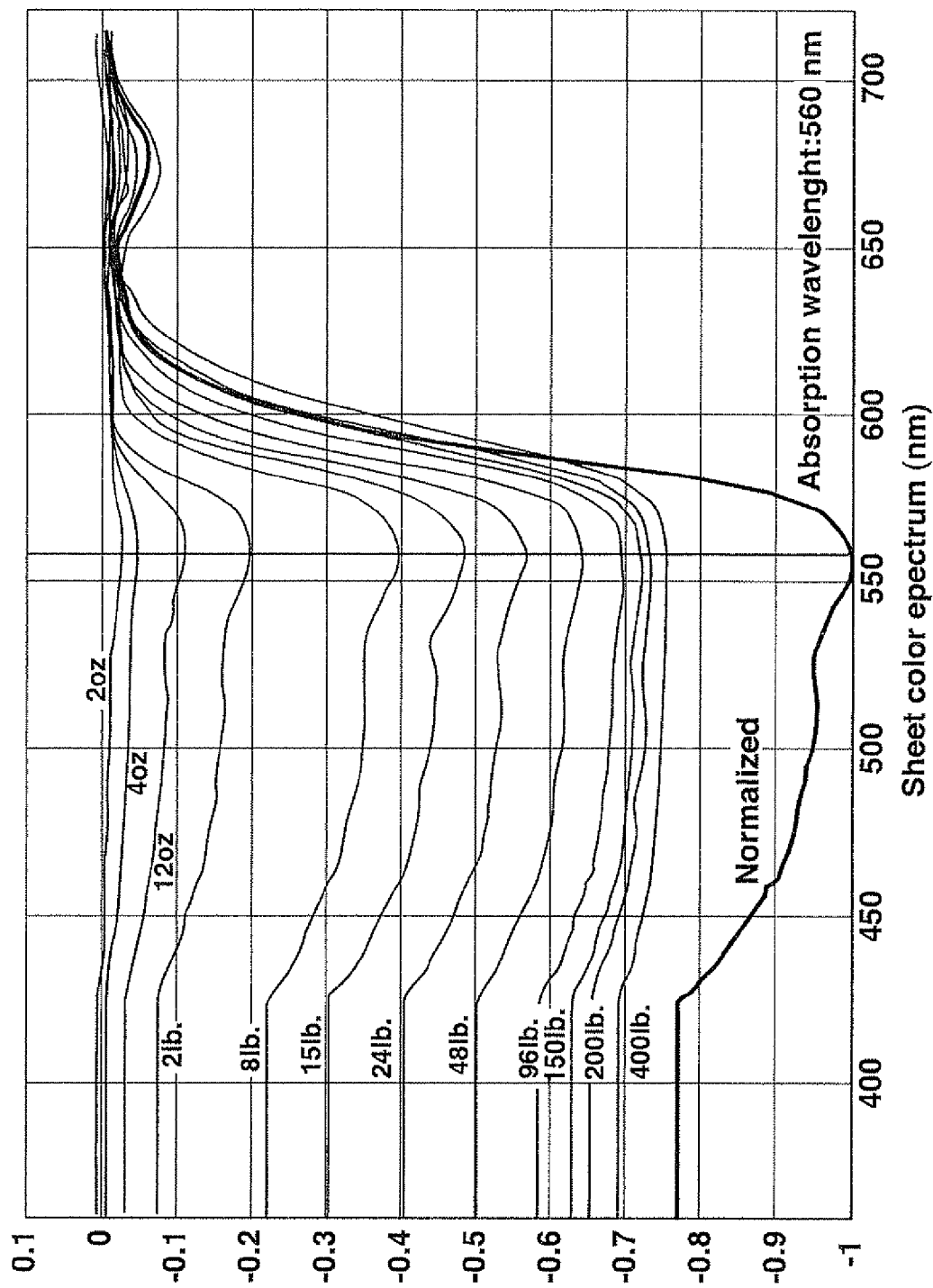
Figure 3C:
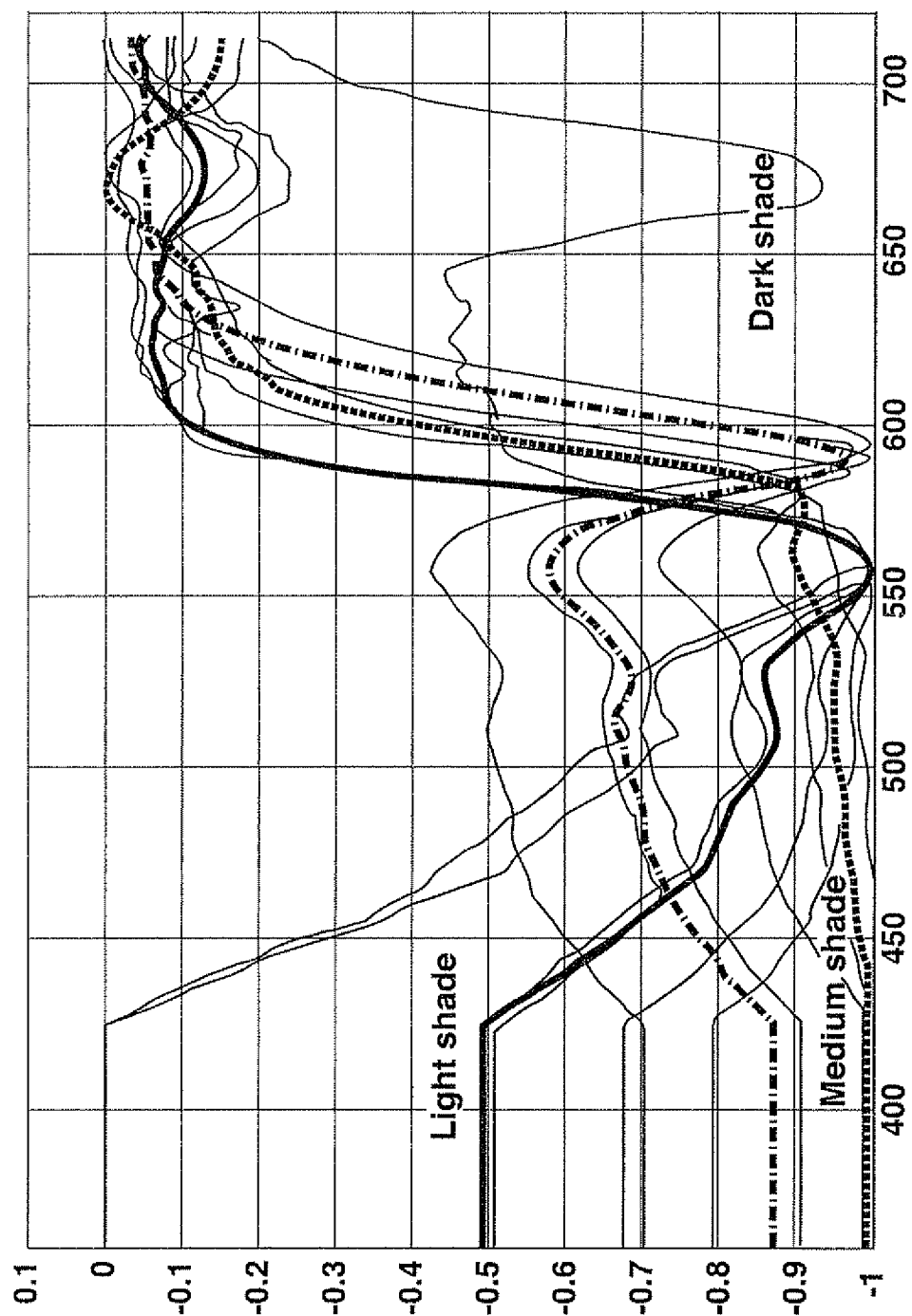
Figure 4:
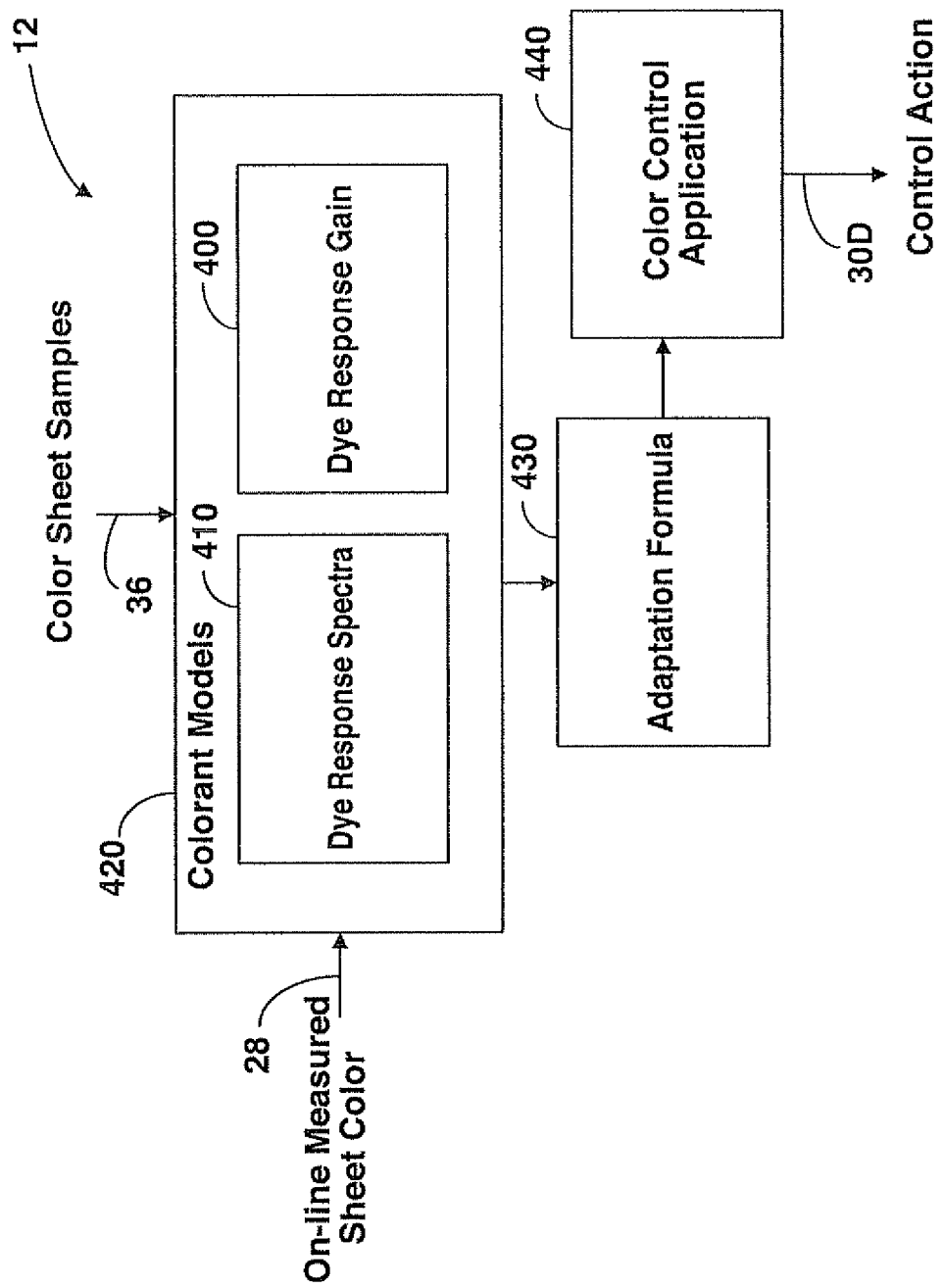
FIG. 4 is a schematic representation of functional components of the controller depicted in FIG. 1 for effecting the coloring process set forth in FIGS. 2 and 3.

Turning now to FIGS. 2-4, additional features of operation of the controller 12 are set forth. First, a-priori off-line measurement is conducted (step 200 in FIG. 2) of the reflectance spectra of pre-specified colour sample sheets (e.g. 12 handsheets) per colorant and OBA's covering a range of concentrations of interest in the manufacturing of a particular color or shade as well as combinations of colorant dosages used for tinting. A measurement of the reflectance spectrum is also taken for a white sample sheet having no colorant. FIG. 3A shows the measured color spectra of the white sample sheet (top) and red samples having different concentrations of dye (from 2 oz/ton to 400 lb/ton), where wavelength is represented by the x-axis and reflectance is represented by the y-axis (with 0 representing 100% absorption and 1 representing 100% reflectance). Measurement values L*, a* and b* for the sample sheets are set forth in Table 1, as follows:

TABLE 1

| Samples of a typical red dye (with different dye concentrations) | | | | | | | | | | | |
|---|---|---|---|---|---|---|---|---|---|---|---|
| | 2 oz | 4 oz | 12 oz | 2 lb | 8 lb | 15 lb | 24 lb | 48 lb | 96 lb | 150 lb | 200 lb | 400 lb |
| L* | 91.6 | 90.8 | 89.0 | 86.2 | 78.1 | 73.5 | 68.7 | 63.0 | 57.7 | 54.9 | 53.1 | 49.4 |
| a* | 0.2 | 1.3 | 4.1 | 8.6 | 20.1 | 26.1 | 34.0 | 41.8 | 48.0 | 51.8 | 53.3 | 55.4 |
| b* | 0.8 | 0.8 | 0.6 | 0.8 | 2.8 | 4.8 | 8.8 | 13.6 | 19.0 | 23.3 | 25.7 | 30.6 |

These measurements are then used to calculate (step 205) a characteristic dye absorption wavelength (i.e. the most negative point in the reflectance spectra difference between a colorant sample sheet and the white sample sheet). More particularly, FIG. 3B shows the calculated spectrum difference between each of the samples in FIG. 3A to the white (base) sheet, along with the averaged and normalized spectrum (where −1 on the y-axis indicates maximum absorption). The characteristic dye absorption wavelength for the illustrated example is approximately 560 nm.

Next, at step 210 a set of colorant and OBA responses is calculated for various dye concentrations. Specifically, the difference between the sample sheet reflectance of each pair of sample sheets (e.g. one such pair being the 8 lb sample and the 24 lb sample from FIG. 3B) is used to calculate a normalized reflectance spectrum difference per unit change in colorant or OBA response (e.g. the response for 16 lb/ton concentration is indicative of the change in dye dosage from 8 lb to 24 lb). This subtraction is performed for each pair of responses in FIG. 3B (normalized to one pound) and the difference is then divided by the difference of their corresponding dosages or concentrations. The resulting response is then further divided by the minimum value of the response (i.e. the process gain) to generate the normalized response depicted in FIG. 3C (i.e. normalized with respect to dosages/concentrations and a minimum value of −1).

Then, at step 215, dye response gains are determined for different reflectance spectrum values at the characteristic absorption wavelength (i.e. adaptation point) for each colorant or OBA. For example, at a concentration of 16 lb/ton, the normalized dye response is as shown in FIG. 3A (a spectrum value of 0.33794 at the 560 nm characteristic dye absorption wavelength) and the response gain is 0.013191. The calculated gain adaptation for the red dye of FIGS. 3A-3C is as set forth in Table 2, and is stored in memory 52 (FIG. 1):

| Reflectance at 560 nm | Gain | Shade |
| --- | --- | --- |
| 0.80447 | 0.24363 | Light |
| 0.79206 | 0.17105 | Light |
| 0.74856 | 0.1466 | Light |
| 0.69301 | 0.090685 | Light |
| 0.56506 | 0.039731 | Light |
| 0.4766 | 0.022157 | Light |
| 0.33794 | 0.013191 | Medium |
| 0.25434 | 0.0075536 | Medium |
| 0.18584 | 0.0024361 | Dark |
| 0.13564 | 0.0015402 | Dark |
| 0.12938 | 0.0011413 | Dark |
| 0.092643 | 0.00057065 | Dark |

In order to minimize the number of normalized response shapes to which a measured sheet reflectance response must be compared (discussed in greater detail below with reference to step 225), the multiple responses in FIG. 3C may be averaged to create three classes of response: light shade, medium shade and dark shade (right-hand column of Table 2). Subsequent on-line adaptation is therefore performed on the basis of similarity between the measured reflectance and a closest one of three responses (e.g. light, medium or dark). This results in reduced computation time for the controller 12 to compute the process model parameters and as well as fewer computer resources required to store the response shapes.

It will be appreciated from the foregoing that the a-priori offline measurement of reflectance spectra of the sample sheets per colorant, according to the off-line or 'setup' steps 200-215, minimizes the need for on-line dye bump tests, and thereby also minimizes generation of off-spec product. The resulting dye response models 420 for use in the production process (steps 220-235 and illustrated in FIG. 4) is therefore composed of the calculated dye absorption wavelength (e.g. 560 nm in FIGS. 3A-3C), a set of normalized response shapes 410 over a spectrum range (e.g. from 360 to 720 nm wavelength) on a scale of from −1 to 0 (e.g. as shown in FIG. 3C), a set of gain adaptation values 400 (e.g. the middle column in Table 2) and the associated reflectance spectrum 410 (e.g. the left-hand column in Table 2). A set of such pre-calculated models 420 is stored in memory 52 for each colorant based on measurement of the sample sheet spectra (36). Optical Brightening Agents (OBAs) are a class of special colorant agent that absorbs energy in ultra violet wavelengths (typically 330 to 380 nm) and release the energy in blue color wavelengths (typically 400 to 450 nm). As a result, the response shape for OBAs can be normalized from −1 to a small positive number (larger than zero). Scaling is also normally done to ensure the reflectance at the red end of the color spectrum is close to zero.

With reference to step 220, the applicable dye response gain is adaptively calculated from the value of the measured sheet spectrum at the dye absorption wavelength, by interpolating between the adaptation gain values of Table 2 that are stored in memory 52.

Next, at step 225, the applicable normalized dye response shape from the sample sheets (i.e. light, medium or dark) is selected using interpolation from the measured sheet reflectance spectrum value at the dye absorption wavelength (i.e. the dye response spectra 410 of the colorant models 420 in FIG. 4). For each response shape, there is an associated sample reflectance spectrum (denoted as $r_s$), which as discussed above, is pre-calculated using the sample sheet reflectance and is used to generate the normalized dye response (i.e. $dr_s/dx$). A normalized response shape (or interpolated response shape) and associated reflectance spectrum (or interpolated reflectance spectrum) are then calculated on-line based on measured sheet reflectance (28) at the characterizing absorption wavelength using the adaptation formula 430.

Then, at step 230, the formula referred to above (identified by reference numeral 430 in FIG. 4) is used for adapting the dye response shape using the measured color spectrum response of the production sheet (denoted as $r_c$). The formula 430 used at step 230 is derived from Kubelka-Munk theory for relating the ratio of total light absorbed and scattered by the sheet to the sum of ratios of light absorbed and scattered by the colorants measured separately. More particularly, it is known from Kubelka-Munk theory that for an opaque sheet (i.e. 100% opacity), the relationship between the ratio y of absorption coefficient K to scattering coefficient S and the reflectance r, is: $y = K/S = (1-r)^2/2r$, where K is related to the absorption of light energy of the sheet; S is related to the light energy scattered backwards by the sheet and the reflectance r is the measured sheet spectrum by the spectrophotometer 50. The rate of change $dr/dx$ of reflectance r to dye ratio, x may be used to define the rate of change of absorption to the dye ratio, as follows: $dy/dx = [(r^2-1)/2r^2](dr/dx)$.

If instead of assuming a constant ratio of reflectance change to dye change, a constant ratio of absorption change to dye change is assumed, then when comparing the sample sheet spectrum $r_s$ and the current sheet spectrum $r_c$, it is possible to adapt current sheet condition dye response shape ($dr_c/dx$) using the dye response from the sample sheet ($dr_s/dx$) by the following formula:

$$\frac{r_c^2 - 1}{2r_c^2} \cdot \frac{dr_c}{dx} = \frac{r_s^2 - 1}{2r_s^2} \cdot \frac{dr_s}{dx}$$

Or, equivalently by the adaptation formula 430:

$$\frac{dr_c}{dx} = \left[\frac{r_s^2 - 1}{2r_s^2}\right] \cdot \left[\frac{dr_s}{dx}\right] / \left[\frac{r_c^2 - 1}{2r_c^2}\right]$$

From the foregoing, it will be appreciated that when the sheet color is light, the reflectance is close to a constant value (as shown in FIG. 3A, white sample to 12 oz red samples) or relatively flat, the change of reflectance by the sample sheet ($dr_s/dx$) would be approximately proportional to the change of response under the current sheet color condition ($dr_c/dx$). However, when the sheet color is dark, it usually has a large variation of the spectrum value, which is accommodated by the adaptation formula 430. The normalized dye response shape associated with the response gain forms the dye response model for generating the color control actions. More particularly, returning to FIG. 2, at step 235, the controller 12 uses a color control application 440 to calculate the optimum control actions 30D based on the dye response for achieving the target color in the shortest possible time.

As discussed above, the colorant models 420 in FIG. 4 include a set of dye response gains 400 (e.g. the exemplary set of adaptation gains for the red dye as indicated in Table 2) and response spectra 410 (as shown in FIG. 3C). It will be appreciated that the dye response spectra 410 use the measured sheet color, a properly selected dye sample spectrum and the corresponding response spectrum of that sample, wherein the selection is based on using the value of measured sheet spectrum at the dye absorption wavelength, and an interpolation method defined by the adaptation formula 430 for the adaptation.

By using the measured sheet reflectance spectrum value (28) at the characteristic absorption wavelength, the response gain for adaptation may be calculated by interpolating or extrapolating the adaptation gain values in Table 2. The normalized response shape and response gain are then used to control the coloring process (step 235) through generation of appropriate control signals 30A and 30D.

In summary, a system and method are provided for sheet color control based on response shape adaptation using the measured sheet reflectance spectrum only, rather than through the use of fixed dye response models as in the prior art (i.e. models that work well only for white or light shade color sheet productions). Such prior art gain adaptation based on fixed dye response shape suffers from disadvantages that are overcome by the system and method set forth herein, such as (i) for a given dye, the response shape when producing different sheet colors can differ with the result that color control action can actually change the color in the wrong direction, (ii) for a given dye concentration, the response gain can be different when making different sheet colors, and (iii) since varying amounts of broke may be used in the paper making process and the broke typically has some amount of color, it is difficult to determine precisely how much 'bias dye flow' must be added as an offset in order to obtain a correct dye response gain.

Specific embodiments have been shown and described herein. However, modifications and variations may occur to those skilled in the art. All such modifications and variations are believed to be within the sphere and scope of the present embodiment.

What is claimed is:

1. A color modeling process for use in manufacturing a colored material using at least one of a colorant or optical brightening agent, comprising:
    a-priori off-line measuring of the reflectance spectra of sample materials covering a range of production colors and determining therefrom a model; and
    on-line measuring of the reflectance spectrum of said colored material and adapting said model according to the measured reflectance spectrum of said colored material at a characteristic absorption wavelength for each said at least one colorant or optical brightening agent, and applying said adapted model for at least one of predicting color trajectory or generating control actions to regulate the flow of said at least one colorant or optical brightening agent.

2. The process of claim 1, wherein said range of production colors corresponds to a range of concentrations of said at least one of colorant or optical brightening agent.

3. The process of claim 2, wherein said model includes (i) said characteristic absorption wavelength, (ii) a set of response shapes and (iii) a set of response gains for said range of concentrations at said characteristic absorption wavelength.

4. The process of claim 3, wherein the set of response shapes is generated by comparing spectra corresponding to two concentrations of said colorant or optical brightening agent, dividing by the difference of their corresponding concentrations and further dividing by a minimum value representing process gain so that said response shapes are normalized with respect to concentration and said minimum value.

5. The process of claim 3, wherein adapting said model further comprises adaptively calculating an appropriate response gain from the measured reflectance spectrum at said characteristic absorption wavelength.

6. The process of claim 3, wherein adapting said model further comprises adaptively calculating an appropriate response model from the measured reflectance spectrum using a selected one of said response shapes at said characteristic absorption wavelength.

7. The process of claim 4, wherein adaptation of said model further is characterized by the formula:

$$\frac{dr_c}{dx} = \left(\frac{r_s^2 - 1}{2r_s^2}\right)\left(\frac{dr_s}{dx}\right) / \left(\frac{r_c^2 - 1}{2r_c^2}\right)$$

where rs represents said set of response shapes, rc represents the measured reflectance spectrum, and drs/dx represents said normalized response shapes.

8. The process of claim 1, wherein generating said control actions includes tinting said material with said colorant.

9. The color modeling process of claim 1, wherein
    in said a-priori off-line measuring step, reflectance spectra of sample sheets covering a range of known concentrations of said at least one of a colorant or optical brightening agent are measured; and
    in said on-line measuring step, said model is used for generating control actions to regulate the flow of said at least one of a colorant or optical brightening agent applied to a color web being the colored material for achieving a target color or brightness.

10. The process of claim 9, wherein said range of concentrations is from zero weight of colorant or optical brightening agent per ton of paper representing a white sample sheet to a concentration representing a darkest shade of said target color or brightness.

11. The process of claim 10, wherein said model includes (i) said characteristic absorption wavelength, (ii) a set of response shapes and (iii) a set of response gains for said range of concentrations at said characteristic absorption wavelength.

12. The process of claim 11, wherein the set of response shapes is generated by comparing spectra corresponding to two concentrations of said colorant or optical brightening agent, dividing by the difference of their corresponding concentrations and further dividing by a minimum value representing process gain so that said response shapes are normalized with respect to concentration and said minimum value.

13. The process of claim 11, wherein adapting said model further comprises adaptively calculating an appropriate response gain from the measured reflectance spectrum at said characteristic absorption wavelength.

14. The process of claim 11, wherein adapting said model further comprises adaptively calculating an appropriate response model from the measured reflectance spectrum using a selected one of said response shapes at said characteristic absorption wavelength.

15. The process of claim 12, wherein adaptation of said model is characterized by the formula:

$$\frac{dr_c}{dx} = \left(\frac{r_s^2 - 1}{2r_s^2}\right)\left(\frac{dr_s}{dx}\right) / \left(\frac{r_c^2 - 1}{2r_c^2}\right)$$

where rs represents said set of response shapes, rc represents the measured reflectance spectrum, and drs/dx represents said normalized response shapes.

16. The process of claim 9, generating said control actions includes tinting said colored web with said colorant.

17. Apparatus for controlling the color of a web of paper, comprising:

a spectrophotometer for scanning said web of paper;
a plurality of regulators; and
a color controller connected to said spectrophotometer and regulators for a-priori off-line measuring of the reflectance spectra of sample sheets covering a range of known concentrations of at least one of a colorant or optical brightening agent and determining therefrom a model, and on-line measuring of the reflectance spectrum of said color paper web and adapting said model according to the measured reflectance spectra of said color paper web at a characteristic absorption wavelength for each said at least one colorant or optical brightening agent, and applying said adapted model for generating and transmitting control actions to said a plurality of regulators for regulating the flow of said at least one of a colorant or optical brightening agent applied to the color web for achieving a target color or brightness.

18. The apparatus of claim 17, wherein said model includes (i) said characteristic absorption wavelength, (ii) a set of response shapes and (iii) a set of response gains for said range of concentrations at said characteristic absorption wavelength.

* * * * *